(12) United States Patent
Flynn et al.

(10) Patent No.: US 7,691,282 B2
(45) Date of Patent: *Apr. 6, 2010

(54) HYDROFLUOROETHER COMPOUNDS AND PROCESSES FOR THEIR PREPARATION AND USE

(75) Inventors: Richard M. Flynn, Mahtomedi, MN (US); Michael G. Costello, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1142 days.

This patent is subject to a terminal disclaimer.

(21) Appl. No.: 11/222,383

(22) Filed: Sep. 8, 2005

(65) Prior Publication Data

US 2007/0051916 A1    Mar. 8, 2007

(51) Int. Cl.
*A62D 1/00* (2006.01)
*C09K 5/00* (2006.01)
*C07C 17/04* (2006.01)
*C07C 19/08* (2006.01)

(52) U.S. Cl. .................... 252/2; 252/67; 252/78.1; 570/136; 570/142; 570/216; 570/246; 570/261; 228/56.3; 134/42; 427/445; 83/13

(58) Field of Classification Search ............... 570/126, 570/142, 216, 246, 261; 252/2, 67, 78.1; 228/56.3; 134/42; 427/445; 83/13
See application file for complete search history.

(56) References Cited

U.S. PATENT DOCUMENTS

| | | |
|---|---|---|
| 3,351,495 A | 11/1967 | Larsen et al. |
| 3,962,348 A | 6/1976 | Benninger et al. |
| 4,539,256 A | 9/1985 | Shipman |
| 4,731,304 A | 3/1988 | Lundquist et al. |
| 5,539,008 A | 7/1996 | Dams et al. |
| 5,565,281 A | 10/1996 | Yu et al. |
| 5,916,708 A | 6/1999 | Besenhard et al. |
| 6,080,448 A | 6/2000 | Leiner et al. |
| 6,203,944 B1 | 3/2001 | Turner et al. |
| 6,255,017 B1 | 7/2001 | Turner |
| 6,342,098 B1 | 1/2002 | Leiner et al. |
| 6,399,729 B1 | 6/2002 | Farnham et al. |
| 6,436,578 B2 | 8/2002 | Turner et al. |
| 6,534,220 B2 | 3/2003 | Garbe |
| 6,680,145 B2 | 1/2004 | Obrovac et al. |
| 6,699,336 B2 | 3/2004 | Turner et al. |
| 6,759,374 B2 | 7/2004 | Milbrath et al. |
| 7,229,718 B2 | 6/2007 | Yamaguchi et al. |
| 2003/0134757 A1 | 7/2003 | Milbrath et al. |
| 2003/0211390 A1 | 11/2003 | Dahn et al. |
| 2004/0038133 A1 | 2/2004 | Yamaguchi et al. |
| 2004/0117918 A1* | 6/2004 | Scheper et al. ............. 8/115.51 |
| 2005/0031957 A1 | 2/2005 | Christensen et al. |
| 2005/0127322 A1 | 6/2005 | Costello et al. |
| 2006/0046144 A1 | 3/2006 | Obrovac |

2007/0054186 A1* 3/2007 Costello et al. .............. 429/200

FOREIGN PATENT DOCUMENTS

| | | |
|---|---|---|
| EP | 0482938 | 4/1992 |
| EP | 0 807 986 A1 | 11/1997 |
| EP | 1 039 570 A1 | 9/2000 |
| JP | 07-249432 | 9/1995 |
| JP | 2002-201152 | 7/2002 |
| JP | 2004-345967 | 12/2004 |
| JP | 2004-363031 | 12/2004 |
| WO | WO 84/02909 | 8/1984 |
| WO | WO 00/03444 | 1/2000 |
| WO | WO 01/27217 A1 | 4/2001 |
| WO | WO 02/102858 A1 | 12/2002 |
| WO | WO 2005/096411 A2 | 10/2005 |
| WO | WO 2006/084096 | 8/2006 |

OTHER PUBLICATIONS

Chambers et al. Israel Journal of Chemisrty (1999), 39(2), 133-140 (abstract from STN search enclosed).*
Nakajima Israel Journal of Fluorine Chemistry (2000), v. 105, 229-238.*
ACS Registry (Registry No. 24556-39-6). 1,1,1,2,3,3-hexafluoro-4-(1,1,2,2-tetrafluoroethoxy)-pentane, Nov. 16, 1984.*
ACS Registry (Registry No. 16627-71-7). 1,1,2,2,3,3,4,4-octafluoro-5-(1,1,2,2-tetrafluoroethoxy)-pentane, Nov. 16, 1984.*
ACS registry (Registry No. 16627-68-2). 1,1,2,2-tetrafluoro-3-(1,1,2,2-tetrafluoroethoxy)-pentane, Nov. 16, 1984.*
Arai, Juichi, "Nonflammable Methyl Nonafluorobutyl Ether for Electrolyte Used in Lithium Secondary Batteries", *Journal of the Electrochemical Society*, 2003, pp. A219-A228.
Costa, Giovanna and Russo, Saverio, "A Comparative Study on Some Fluoroalcohols as Potential Solvents for Aliphatic Polyamides", *J. Macromol. Sci.-Chem.*, 1982, pp. 299-312.
Nakajima, Tsuyoshi; Dan, Koh-ichi; Koh, Meiten; Ino, Tadashi; Shimizu, Tetsuo; "Effect of Addition of Fluoroethers to Organic Solvents for Lithium Ion Secondary Batteries", *Journal of Fluorine Chemistry*, 2001, pp. 167-174.
Il'in et al., "Synthesis and Use of Partially Fluorinated Diakyl Ethers Derived from Hexafluoropropylene", Russian Journal of Applied Chemistry, Publisher: MAIK Nauka/Interperiodica, distributed exclusively by Springer Science+Business Media LLC.; ISSN: 1070-4272 (Paper) 1608-3296 (Online) DOI: 10.1023/B:RJAC. 0000024585.14553.5f ; Issue: vol. 77, No. 1 Date: Jan. 2004; pp. 98-101.

(Continued)

*Primary Examiner*—Lorna M Douyon
*Assistant Examiner*—Amina Khan
(74) *Attorney, Agent, or Firm*—Lucy C. Weiss

(57) ABSTRACT

Disclosed is a hydrofluoroether compound comprising two terminal fluoroalkyl groups and an intervening substituted or unsubstituted oxymethylene group, each of the fluoroalkyl groups comprising only one hydrogen atom and, optionally, at least one catenated (that is, in-chain) heteroatom; with the proviso that the hydrogen atom is part of a monofluoromethylene moiety.

23 Claims, No Drawings

CAN 141:175792 AN 2004:87037 CAPLUS (Copyright 2005 ACS on SciFinder (R)) Ilyin et al., "The use of tetrafluoroethylene and hexafluoropropylene in the synthesis of partly fluorinated alcohols and dialkyl ethers"; Fluorine Notes (2003), 30 Paper No. 1, No pp. given, Paper No. 1. CODEN: FNLOA7; Online Computer Filed written in English.

"Addition reactions of fluororalkyl ethyl ethers to perfluoropropene"; Muramatsu, Hiroshige; Kimoto, Hiroshi; Inukai, Kan. Govt. Ind. Res. Inst., Nagoya, Japan; Bulletin of the Chemical Society of Japan (1969), 42(4), 1155-8; CODEN: BCSJA8 ISSN: 0009-2673. Journal written in English CAN 71:21635 AN 1969:421635 CAPLUS (Copyright 2005 ACS on SciFinder (R)).

Chambers R D et al., "Free Radical Chemistry. Part 3.1 Substituent Effects in Additions of Ethers to Fluorinated Alkenes", Journal of the Chemical Society. Perkin Transactions 1, Chemical Society, Letchworth, GB, No. 1, 1985, pp. 2209-2213, XP002926087 ISSN: 0300-922X.

Davies, "Metallic glass formation", *Amorphous Metallic Alloys*, Chapter 2, pp. 8-25, F. E. Luborsky, ed., Butterworth & Co., 1983.

Chi et al., "A Facile Synthesis of Partly-fluorinated Ethers Using Perfluoropropoxyethylene and Aliphatic Alcohols", *Bull. Korean Chem. Soc.*, vol. 20, No. 2, 1999, pp. 220-222.

Nakajima, "Fluorine-containing energy conversion materials", *Journal of Fluorine Chemistry* 105 (2000), pp. 229-238.

Gavelin et al., "Amphiphilic solid polymer electrolytes", *Solid State Ionics* 147 (2002), pp. 325-332.

Kyokane et al., "Electrical properties of fluorinated gel electrolytes using high ionic conducting solution and its application to secondary battery", *Thin Solid Films* 438-439 (2003), pp. 257-261.

Balakrishnan et al., "Safety mechanisms in lithium-ion batteries", *Journal of Power Sources* 155 (2006), pp. 401-414.

* cited by examiner

HYDROFLUOROETHER COMPOUNDS AND PROCESSES FOR THEIR PREPARATION AND USE

FIELD

This invention relates to partially-fluorinated ether compounds. In other aspects, this invention also relates to processes for preparing partially-fluorinated ether compounds and to processes for their use.

BACKGROUND

Hydrofluoroether compounds (HFEs) comprise a class of commercially valuable chemical compounds. In a number of applications, hydrofluoroethers have been found to be useful as replacements for chlorofluorocarbons (CFCs), which are currently disfavored and regulated due to the adverse effects that CFCs are believed to have on the environment. Hydrofluoroether compounds have been found to be less harmful to the earth's ozone layer than CFCs because, for example, they are typically more easily degraded within the earth's atmosphere. Thus, hydrofluoroether compounds are said to exhibit a low "ozone depletion potential".

Hydrofluoroether compounds have been prepared by various different methods including, for example, alkylation of perfluorinated acid fluorides (prepared by electrochemical fluorination or by direct fluorination), alkylation of perfluorinated ketones (prepared by reaction of perfluorinated acid fluorides and perfluorinated olefins), and photooxidation of tetrafluoroethylene (TFE). Such methods have various advantages and disadvantages. For example, the latter method requires the handling of a relatively hazardous reagent, TFE, and also provides a broad product mixture that generally requires extensive purification.

SUMMARY

In view of an increasing demand for environmentally friendly chemical compounds, we recognize that there exists an ongoing need for HFEs that can meet the performance requirements of a variety of different applications, as well as for efficient and cost-effective processes for their preparation. Such processes will preferably be capable of flexibly and controllably producing hydrofluoroether compounds having tailored structures and physical properties, without producing a broad product mixture.

Briefly, in one aspect, this invention provides a hydrofluoroether compound comprising two terminal fluoroalkyl groups and an intervening substituted or unsubstituted oxymethylene group, each of the fluoroalkyl groups comprising only one hydrogen atom and, optionally, at least one catenated (that is, in-chain) heteroatom; with the proviso that the hydrogen atom is part of a monofluoromethylene moiety. Preferably, the oxymethylene group is substituted (that is, at least one carbon-bonded hydrogen atom is replaced with an alkyl or fluoroalkyl group that optionally contains at least one catenated heteroatom).

It has been discovered that a versatile new class of normally liquid hydrofluoroether compounds can be flexibly produced by a simple process comprising typically sequential free radical and anionic additions of perfluoroolefins (or perfluorovinyl ethers) to alcohols. By varying the nature of the starting materials and the order of the addition steps, HFEs having tailored structures and physical properties can be controllably obtained.

The HFEs of the invention can be used in a number of different applications including, for example, use as a solvent in coating deposition, as a cleaning or drying fluid, as a dry cleaning fluid, as a polymerization medium, as a fire extinguishing medium, as a document preservation medium, as a heat transfer agent, as a cell size regulator for use in foam blowing, as a heat transfer agent for use in vapor phase soldering, and as a metal working agent in the cutting or forming of metals. At least some of the HFEs exhibit unexpectedly high thermal stabilities, making them particularly useful in high temperature applications. Thus, at least some embodiments of the invention meet the above-described, ongoing need for HFEs that can meet the performance requirements of a variety of different applications (as well as the need for efficient and cost-effective processes for their preparation).

In another aspect, this invention also provides a process for preparing the hydrofluoroether compounds comprising (a) providing (1) at least one perfluoroolefin or perfluorovinyl ether starting compound that optionally contains at least one catenated heteroatom and (2) at least one hydrocarbon or addition-capable fluorocarbon alcohol that is monofunctional or polyfunctional (preferably, monofunctional) and that optionally contains at least one catenated heteroatom; (b) effecting a free radical type of addition reaction or an anionic type of addition reaction of the starting compound and the alcohol to form at least one first fluoroalcohol intermediate; (c) providing at least one perfluoroolefin or perfluorovinyl ether finishing compound that is the same as or different from the starting compound; and (d) effecting an anionic type of addition reaction or a free radical type of addition reaction of the finishing compound and the first fluoroalcohol intermediate to form at least one second fluoroalcohol intermediate (if a polyfunctional alcohol is utilized and an anionic addition reaction is effected in step (b)) or at least one hydrofluoroether compound; with the proviso that the addition reactions of steps (b) and (d) differ in type; and with the further proviso that, when the alcohol is a monofunctional alcohol, the addition reaction of step (b) is a free radical type addition reaction.

Preferably, the free radical addition reaction is carried out first, even when a polyfunctional alcohol is utilized. Otherwise, the use of a polyfunctional alcohol generally involves an additional step (e), in which an anionic type of addition reaction is effected to convert the second fluoroalcohol intermediate to a hydrofluoroether compound.

In still other aspects, this invention provides the following processes for using the hydrofluoroether compounds of the invention:

A process for removing a contaminant (for example, an oil or grease, a particulate, or water) from an article comprising contacting the article with a composition comprising at least one hydrofluoroether compound of the invention.

A process for the extinction of fires comprising applying to a fire a composition comprising at least one hydrofluoroether compound of the invention.

A process for preparing a foamed plastic comprises vaporizing a blowing agent mixture in the presence of at least one foamable polymer or the precursors of at least one foamable polymer, the blowing agent mixture comprising at least one hydrofluoroether compound of the invention.

A process for vapor phase soldering comprising melting solder by immersing at least one component that comprises solder in a body of fluorinated liquid vapor that comprises at least one hydrofluoroether compound of the invention.

A process for transferring heat comprising transferring heat between a heat source and a heat sink through the use of a heat transfer agent comprising at least one hydrofluoroether compound of the invention.

A process for depositing a coating on a substrate comprising applying to at least a portion of at least one surface of the substrate a composition comprising (a) a solvent composition comprising at least one hydrofluoroether compound of the invention; and (b) at least one coating material (for example, a fluorinated polyether or a document preservation material) that is soluble or dispersible in the solvent composition.

A process for metal, cermet, or composite working comprising applying a working fluid to a metal, cermet, or composite workpiece and tool, the working fluid comprising at least one hydrofluoroether compound of the invention and at least one lubricious additive.

A polymerization process comprising polymerizing at least one monomer (preferably, a fluorine-containing monomer) in the presence of at least one polymerization initiator and at least one hydrofluoroether compound of the invention.

DETAILED DESCRIPTION

Definitions

As used in this patent application:

"addition-capable" (in regard to a fluorocarbon alcohol) means an alcohol in which the carbon-bonded fluorine is sufficiently distant from the hydroxyl group to enable the addition reaction with starting compound to occur;

"catenated heteroatom" means an atom other than carbon (for example, oxygen, nitrogen, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"monofunctional" or "polyfunctional" (in regard to an alcohol) means that the alcohol contains only one hydroxyl group or at least two hydroxyl groups, respectively;

"normally liquid" means liquid under ambient conditions of temperature and pressure (for example, at about 20° C. and about 1 atmosphere);

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine; and "substituted" (in reference to a group or moiety) means that at least one carbon-bonded hydrogen atom is replaced with an alkyl or fluoroalkyl group that optionally contains one or more catenated heteroatoms.

Hydrofluoroether Compounds

The novel compounds of the invention comprise two terminal fluoroalkyl groups and an intervening substituted or unsubstituted oxymethylene group ($-CR_1R_2-O-$, wherein $R_1$ and $R_2$ are independently hydrogen or a substituent group defined below), each of the fluoroalkyl groups comprising only one hydrogen atom and, optionally, comprising at least one catenated (that is, in-chain) heteroatom; with the proviso that the hydrogen atom is part of a monofluoromethylene moiety. Preferably, the oxymethylene group is substituted (that is, at least one carbon-bonded hydrogen atom is replaced with an alkyl or fluoroalkyl group that can optionally contain one or more catenated heteroatoms).

A class of the compounds of the invention is that which can be represented by the following general formula (I):

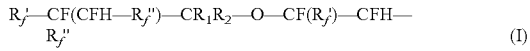

$$R_f'-CF(CFH-R_f'')-CR_1R_2-O-CF(R_f')-CFH-R_f'' \qquad (I)$$

wherein each $R_f'$ is independently a fluorine atom or a perfluoroalkyl group that is linear, branched, cyclic, or a combination thereof and that optionally contains at least one catenated heteroatom; each $R_f''$ is independently a perfluoroalkyl group that is linear, branched, cyclic, or a combination thereof and that optionally contains at least one catenated heteroatom; and $R_1$ and $R_2$ are independently a hydrogen atom, an alkyl group that is linear, branched, cyclic, or a combination thereof and that optionally contains at least one catenated heteroatom, or a fluoroalkyl group that is linear, branched, cyclic, or a combination thereof and that optionally contains at least one catenated heteroatom. Preferably, $R_1$ is hydrogen or an alkyl group that is linear, branched, cyclic, or a combination thereof; and $R_2$ is hydrogen or an alkyl group that is linear, branched, cyclic, or a combination thereof, or is a moiety that can be represented by the formula $-(CR_1R_3)_n-O-CF(R_f')-CFH-R_f''$, where $R_3$ is hydrogen or an alkyl group that is linear, branched, cyclic, or a combination thereof, or is a moiety that can be represented by the formula $-CF(R_f')-CFH-R_f''$, and n is an integer of 1 to about 8. More preferably, $R_1$ is hydrogen or an alkyl group that is linear, branched, cyclic, or a combination thereof; and $R_2$ is an alkyl group that is linear, branched, cyclic, or a combination thereof. Most preferably, $R_1$ is hydrogen or an alkyl group having up to about three carbon atoms (preferably, the alkyl group is a methyl group), and $R_2$ is an alkyl group having up to about three carbon atoms (preferably, a methyl group). Preferably, each $R_f'$ is independently fluorine or $C_3F_7-$ (more preferably, fluorine); and each $R_f''$ is independently selected from $C_3F_7O-$, $C_4F_9O-$, $C_3F_7OC_3F_6O-$, $CF_3OC_3F_6O-$, and $CF_3-$ (more preferably, $CF_3-$).

Representative examples of the hydrofluoroether compounds of the invention include the following:

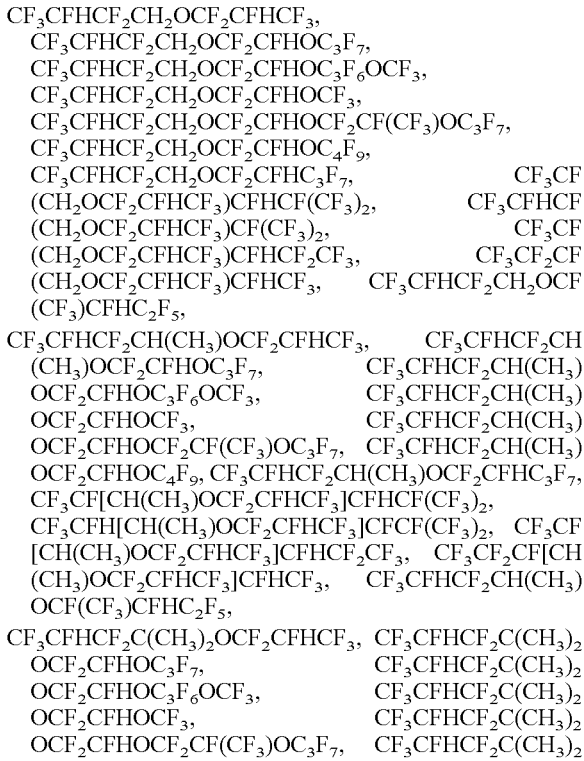

$CF_3CFHCF_2CH_2OCF_2CFHCF_3$,
$CF_3CFHCF_2CH_2OCF_2CFHOC_3F_7$,
$CF_3CFHCF_2CH_2OCF_2CFHOC_3F_6OCF_3$,
$CF_3CFHCF_2CH_2OCF_2CFHOCF_3$,
$CF_3CFHCF_2CH_2OCF_2CFHOCF_2CF(CF_3)OC_3F_7$,
$CF_3CFHCF_2CH_2OCF_2CFHOC_4F_9$,
$CF_3CFHCF_2CH_2OCF_2CFHC_3F_7$, $CF_3CF(CH_2OCF_2CFHCF_3)CFHCF(CF_3)_2$, $CF_3CFHCF(CH_2OCF_2CFHCF_3)CF(CF_3)_2$, $CF_3CF(CH_2OCF_2CFHCF_3)CFHCF_2CF_3$, $CF_3CF_2CF(CH_2OCF_2CFHCF_3)CFHCF_3$, $CF_3CFHCF_2CH_2OCF(CF_3)CFHC_2F_5$,
$CF_3CFHCF_2CH(CH_3)OCF_2CFHCF_3$, $CF_3CFHCF_2CH(CH_3)OCF_2CFHOC_3F_7$, $CF_3CFHCF_2CH(CH_3)OCF_2CFHOC_3F_6OCF_3$, $CF_3CFHCF_2CH(CH_3)OCF_2CFHOCF_3$, $CF_3CFHCF_2CH(CH_3)OCF_2CFHOCF_2CF(CF_3)OC_3F_7$, $CF_3CFHCF_2CH(CH_3)OCF_2CFHOC_4F_9$, $CF_3CFHCF_2CH(CH_3)OCF_2CFHCF_3$, $CF_3CF[CH(CH_3)OCF_2CFHCF_3]CFHCF(CF_3)_2$, $CF_3CFH[CH(CH_3)OCF_2CFHCF_3]CFCF(CF_3)_2$, $CF_3CF[CH(CH_3)OCF_2CFHCF_3]CFHCF_2CF_3$, $CF_3CF_2CF[CH(CH_3)OCF_2CFHCF_3]CFHCF_3$, $CF_3CFHCF_2CH(CH_3)OCF(CF_3)CFHC_2F_5$,
$CF_3CFHCF_2C(CH_3)_2OCF_2CFHCF_3$, $CF_3CFHCF_2C(CH_3)_2OCF_2CFHOC_3F_7$, $CF_3CFHCF_2C(CH_3)_2OCF_2CFHOC_3F_6OCF_3$, $CF_3CFHCF_2C(CH_3)_2OCF_2CFHOCF_3$, $CF_3CFHCF_2C(CH_3)_2OCF_2CFHOCF_2CF(CF_3)OC_3F_7$, $CF_3CFHCF_2C(CH_3)_2$

OCF$_2$CFHOC$_4$F$_9$, CF$_3$CFHCF$_2$C(CH$_3$)$_2$OCF$_2$CFHC$_3$F$_7$, CF$_3$CF[C(CH$_3$)$_2$OCF$_2$CFHCF$_3$]CFHCF$_2$CF$_3$, CF$_3$CF$_2$CF[C(CH$_3$)$_2$OCF$_2$CFHCF$_3$]CFHCF$_3$,
C$_3$F$_7$OCFHCF$_2$CH$_2$OCF$_2$CFHCF$_3$,
 C$_3$F$_7$OCFHCF$_2$CH$_2$OCF$_2$CFHOC$_3$F$_7$,
C$_3$F$_7$OCFHCF$_2$CH$_2$OCF$_2$CFHOC$_3$F$_6$OCF$_3$,
 C$_3$F$_7$OCFHCF$_2$CH$_2$OCF$_2$CFHOCF$_3$,
 C$_3$F$_7$OCFHCF$_2$CH$_2$OCF$_2$CFHOCF$_2$CF(CF$_3$)OC$_3$F$_7$,
 C$_3$F$_7$OCFHCF$_2$CH$_2$OCF$_2$CFHOC$_4$F$_9$,
 C$_3$F$_7$OCFHCF$_2$CH$_2$OCF$_2$CFHC$_3$F$_7$, CF$_3$CF(CH$_2$OCF$_2$CFHOC$_3$F$_7$)CFHCF(CF$_3$)$_2$, CF$_3$CF(CH$_2$OCF$_2$CFHOC$_3$F$_7$)CFHCF$_2$CF$_3$, CF$_3$CF$_2$CF(CH$_2$OCF$_2$CFHOC$_3$F$_7$)CFHCF$_3$,
C$_3$F$_7$OCFHCF$_2$CH(CH$_3$)OCF$_2$CFHCF$_3$,
 C$_3$F$_7$OCFHCF$_2$CH(CH$_3$)OCF$_2$CFHOC$_3$F$_7$,
 C$_3$F$_7$OCFHCF$_2$CH(CH$_3$)OCF$_2$CFHOC$_3$F$_6$OCF$_3$,
 C$_3$F$_7$OCFHCF$_2$CH(CH$_3$)OCF$_2$CFHOCF$_3$,
 C$_3$F$_7$OCFHCF$_2$CH(CH$_3$)OCF$_2$CFHOCF$_2$CF(CF$_3$)OC$_3$F$_7$, C$_3$F$_7$OCFHCF$_2$CH(CH$_3$)OCF$_2$CFHOC$_4$F$_9$,
 C$_3$F$_7$OCFHCF$_2$CH(CH$_3$)OCF$_2$CFHC$_3$F$_7$, CF$_3$CF(CH(CH$_3$)OCF$_2$CFHOC$_3$F$_7$)CFHCF(CF$_3$)$_2$, CF$_3$CF(CH(CH$_3$)OCF$_2$CFHOC$_3$F$_7$)CFHCF$_2$CF$_3$, CF$_3$CF$_2$CF(CH(CH$_3$)OCF$_2$CFHOC$_3$F$_7$)CFHCF$_3$,
C$_3$F$_7$OCFHCF$_2$C(CH$_3$)$_2$OCF$_2$CFHCF$_3$, C$_3$F$_7$OCFHCF$_2$C(CH$_3$)$_2$OCF$_2$CFHOC$_3$F$_7$, C$_3$F$_7$OCFHCF$_2$C(CH$_3$)$_2$OCF$_2$CFHOC$_3$F$_6$OCF$_3$, C$_3$F$_7$OCFHCF$_2$C(CH$_3$)$_2$OCF$_2$CFHOCF$_3$, C$_3$F$_7$OCFHCF$_2$C(CH$_3$)$_2$OCF$_2$CFHOCF$_2$CF(CF$_3$)OC$_3$F$_7$, C$_3$F$_7$OCFHCF$_2$C(CH$_3$)$_2$ OCF$_2$CFHOC$_4$F$_9$, C$_3$F$_7$OCFHCF$_2$C(CH$_3$)$_2$OCF$_2$CFHC$_3$F$_7$, CF$_3$CF(C(CH$_3$)$_2$OCF$_2$CFHOC$_3$F$_7$)CF-HCF(CF$_3$)$_2$, CF$_3$CF(C(CH$_3$)$_2$OCF$_2$CFHOC$_3$F$_7$)CFHCF$_2$CF$_3$, CF$_3$CF$_2$CF(C(CH$_3$)$_2$OCF$_2$CFHOC$_3$F$_7$)CF-HCF$_3$,
CF$_3$CFHCF$_2$CH(OCF$_2$CFHCF$_3$)CH$_2$OCF$_2$CFHCF$_3$, CF$_3$OCF(CF$_3$)CF$_2$OCFHCF$_2$C(CH$_3$)$_2$OCF$_2$CFHCF$_3$, [CF$_3$CFHCF$_2$OCH(CF$_2$CFHCF$_3$)]$_2$CH$_2$,
 CF$_3$CFHCF$_2$OCH$_2$CH$_2$CH(CF$_2$CFHCF$_3$)OCF$_2$CFHCF$_3$, C$_4$F$_9$CH$_2$CH(CF$_2$CFHCF$_3$)OCF$_2$CFHCF$_3$, CH$_3$C(OCF$_2$CFHCF$_3$)(CF$_2$CFHCF$_3$)CH$_2$OCF$_2$CFHCF$_3$, CH$_3$CH(OCF$_2$CFHCF$_3$)CH(OCF$_2$CFHCF$_3$)CF$_2$CFHCF$_3$,

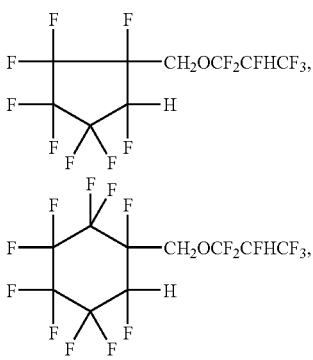

and the like, and mixtures thereof.

Preferred hydrofluoroether compounds include CF$_3$CFHCF$_2$CH(CH$_3$)OCF$_2$CFHCF$_3$,
 CF$_3$CFHCF$_2$CH$_2$OCF$_2$CFHCF$_3$,
 CF$_3$CFHCF$_2$CH$_2$OCF$_2$CFHOC$_4$F$_9$, C$_3$F$_7$OCFHCF$_2$CH(CH$_3$)OCF$_2$CFHCF$_3$, CF$_3$CFH[CH(CH$_3$)OCF$_2$CFHCF$_3$]CFCF(CF$_3$)$_2$, CF$_3$CFHCF$_2$CH(OCF$_2$CFHCF$_3$)CH$_2$OCF$_2$CFHCF$_3$, CF$_3$CFHCF$_2$CH$_2$OCF$_2$CFHOC$_3$F$_7$,
 CF$_3$CFHCF$_2$CH$_2$OCF$_2$CFHOCF$_3$, CF$_3$CF(CH$_2$OCF$_2$CFHCF$_3$)CFHCF(CF$_3$)$_2$, CF$_3$CFHCF(CH$_2$OCF$_2$CFHCF$_3$)CF(CF$_3$)$_2$, CF$_3$CFHCF$_2$CH(CH$_3$)OCF$_2$CFHCF$_3$, CF$_3$CF[CH(CH$_3$)OCF$_2$CFHCF$_3$]CFHCF(CF$_3$)$_2$, CF$_3$CF[CH(CH$_3$)OCF$_2$CFHCF$_3$]CFHCF$_2$CF$_3$, CF$_3$CF$_2$CF[CH(CH$_3$)OCF$_2$CFHCF$_3$]CFHCF$_3$, CF$_3$CFHCF$_2$C(CH$_3$)$_2$OCF$_2$CFHCF$_3$, CF$_3$CFHCF$_2$C(CH$_3$)$_2$OCF$_2$CFHOC$_3$F$_7$,
 C$_3$F$_7$OCFHCF$_2$CH$_2$OCF$_2$CFHCF$_3$, CF$_3$OCF(CF$_3$)CF$_2$OCFHCF$_2$C(CH$_3$)$_2$OCF$_2$CFHCF$_3$, CF$_3$CFHCF$_2$OCH$_2$CH$_2$CH(CF$_2$CFHCF$_3$)OCF$_2$CFHCF$_3$,
and mixtures thereof; with
CF$_3$CFHCF$_2$CH(CH$_3$)OCF$_2$CFHCF$_3$, CF$_3$CFH[CH(CH$_3$)OCF$_2$CFHCF$_3$]CFCF(CF$_3$)$_2$,CF$_3$CF[CH(CH$_3$)OCF$_2$CFHCF$_3$]CFHCF$_2$CF$_3$, CF$_3$CFHCF$_2$CH(OCF$_2$CFHCF$_3$)CH$_2$OCF$_2$CFHCF$_3$, and mixtures thereof being more preferred.

The hydrofluoroether compounds of the invention are hydrophobic and less oleophobic than their perfluoroether analogs, relatively chemically unreactive, thermally stable, water insoluble, and normally liquid (for example, at 20° C.), and they can be made in accordance with this invention in high yield, high purity, and with a wide range of molecular weights. Their covalent carbon-hydrogen bonds are generally degradable by atmospheric photo-oxidation, thus making the hydrofluoroether compounds environmentally acceptable or compatible.

Preparation of Hydrofluoroether Compounds

The hydrofluoroether compounds of the invention can be prepared by first effecting a free radical addition of at least one perfluoroolefin or perfluorovinyl ether starting compound and at least one hydrocarbon or addition-capable fluorocarbon alcohol. This results in the formation of at least one fluoroalcohol intermediate. The fluoroalcohol intermediate can then be anionically added to at least one perfluoroolefin or perfluorovinyl ether finishing compound (which can be the same as or different from the perfluoroolefin or perfluorovinyl ether used in the first addition reaction) to form at least one hydrofluoroether compound. Alternatively, when the alcohol is polyfunctional, the types of addition reactions can be reversed, with the first addition being an anionic addition and the second being a free radical addition. The order of the steps is thus non-limiting and can be modified so as to produce a desired chemical composition.

Perfluoroolefins that are useful in carrying out the preparation process of the invention include those that contain at least one carbon atom bonded to one of the carbon atoms of the olefinic double bond. Useful perfluorovinyl ethers include those that possess a terminal difluoromethylene group as part of the olefinic double bond. Such perfluoroolefins and perfluorovinyl ethers, which optionally can further contain one or more catenated heteroatoms (in addition to the ether oxygen of the perfluorovinyl ethers), provide product hydrofluoroether compounds that are generally characterized by the absence of hydrogen atoms bonded to primary (terminal) carbon atoms. In addition, the resulting hydrofluoroether compounds characteristically comprise hydrogen in the form of at least two monofluoromethylene (—CFH—) moieties.

The perfluoroolefin starting compounds can be prepared by any of a variety of standard synthetic procedures that are well-known in the art. The perfluorovinyl ether starting compounds can be prepared by the reaction of a perfluorinated acyl fluoride or a perfluorinated ketone with hexafluoropropylene oxide (HFPO) to form an intermediate branched acyl fluoride adduct. This adduct can then be reacted with a base to form an intermediate carboxylic acid salt, which can then be decarboxylated at elevated temperature (optionally, in the presence of an inert solvent). Some perfluoroolefins and perfluorovinyl ethers (for example, $CF_3CF=CF_2$, $C_5F_{11}CF=CF_2$, $C_3F_7OCF=CF_2$, $C_3F_7OCF(CF_3)$ $CF_2OCF=CF_2$, $CF_3CF=CFC_2F_5$, $CF_3OCF=CF_2$, $(CF_3)_2CFCF=CFCF_3$. perfluorocyclobutene, perfluorocyclopentene, and perfluorocyclohexene) are also commercially available (for example, from Synquest or from Apollo Scientific, Ltd.).

Representative examples of perfluoroolefins that are useful in preparing the hydrofluoroether compounds include $CF_3CF=CF_2$, $C_3F_7CF=CF_2$, $C_3F_7OCF_2CF=CF_2$, $CF_3CF_2CF=CF_2$, $(CF_3)_2CFCF=CFCF_3$, $(CF_3)_2NC_3F_6OCF_2CF=CF_2$, $CF_3CF=CFC_2F_5$, perfluorocyclopentene, perfluorocyclobutene, perfluorocyclohexene, and the like, and mixtures thereof. (Mixtures of starting compounds and/or mixtures of finishing compounds can be used, if desired, but mixtures are generally less preferred due to the resulting production of product mixtures that can require purification.) Preferred perfluoroolefins include $CF_3CF=CF_2$, $(CF_3)_2CFCF=CFCF_3$, $CF_3CF=CFC_2F_5$, and mixtures thereof. $CF_3CF=CF_2$, $(CF_3)_2CFCF=CFCF_3$, and mixtures thereof are more preferred.

Representative examples of perfluorovinyl ethers that are useful in preparing the hydrofluoroether compounds include $C_3F_7OCF=CF_2$, $C_3F_7OCF(CF_3)CF_2OCF=CF_2$, $CF_3OCF=CF_2$, $C_4F_9OCF=CF_2$, $CF_3OC_3F_6OCF=CF_2$, and the like, and mixtures thereof. Preferred perfluorovinyl ethers include $C_3F_7OCF=CF_2$, $C_4F_9OCF=CF_2$, $CF_3OC_3F_6OCF=CF_2$, and mixtures thereof. $C_3F_7OCF=CF_2$, $C_4F_9OCF=CF_2$, and mixtures thereof are more preferred.

Alcohols that are useful in carrying out the preparation process of the invention include those that have at least one free radically abstractable hydrogen atom located alpha to the hydroxyl group (that is, bonded to the carbon atom that is bonded to the hydroxyl group). Such alcohols include both hydrocarbon alcohols and fluorocarbon alcohols (for example, those that can be represented by the general formula $R_fC_2H_4OH$, wherein $R_f$ is a perfluoroalkyl or fluoroalkyl group that optionally contains at least one catenated heteroatom and that preferably contains from one to about twelve carbon atoms). The alcohols can be monofunctional or polyfunctional and, optionally, can contain one or more catenated heteroatoms.

Such alcohols are generally commercially available and provide product hydrofluoroether compounds that comprise a substituted or unsubstituted oxymethylene group. Hydrocarbon alcohols can be preferred due to their relatively lower cost (in comparison with fluorocarbon alcohols), although preferred alcohols are generally those that provide product HFE compounds that are non-flammable. Thus, more preferred are hydrocarbon alcohols having no more than about six carbon atoms (most preferably, no more than about three carbon atoms).

Representative examples of suitable alcohols include methanol, ethanol, isopropanol, ethylene glycol, 1-propanol, 1-butanol, 2-butanol, 2-methyl-1-propanol, 2-methoxyethanol, 1,2-propanediol, 1,3-propanediol, glycerol, $(CH_3)_2NC_2H_4OH$, $C_4F_9CH_2CH_2OH$, $C_4F_9CH_2CH_2CH_2OH$, $C_8F_{17}CH_2CH_2CH_2OH$, $C_4F_9OCH_2CH_2OH$, and the like, and mixtures thereof. Preferred alcohols include methanol, ethanol, isopropanol, 1,3-propanediol, ethylene glycol, and mixtures thereof. Methanol, ethanol, isopropanol, and mixtures thereof are more preferred.

The free radical addition reaction can be effected by combining the perfluoroolefin or perfluorovinyl ether starting compound and the alcohol (or the fluoroalcohol intermediate) in the presence of at least one free radical initiator. Suitable free radical initiators include peroxides, peroxyesters, peroxycarbonates, and the like, and mixtures thereof. Examples of such initiators include t-amylperoxy-2-ethylhexanoate (available as LUPEROX 575 from Arkema, Crosby, Tex.), lauryl peroxide, t-butyl peroxide, t-amylperoxy-2-ethylhexyl carbonate, and mixtures thereof, with t-amylperoxy-2-ethylhexanoate being a preferred initiator.

For example, liquid starting compound, excess alcohol, and the initiator can be combined in any order in a reactor (for example, a pressure reactor), which can then be heated to a desired reaction temperature (for example, from about 50° C. to about 120° C.) under autogenous pressure (and generally with stirring or agitation). Solvents that are not very reactive under the reaction conditions (for example, methyl isobutyl ketone or a hydrofluoroether compound such as a NOVEC brand fluid available from 3M Company, St. Paul, Minn.) can be utilized, if desired, but are generally not needed due to the presence of the alcohol reactant.

When a gaseous starting compound (for example, hexafluoropropylene or $CF_3OCF=CF_2$) is utilized, the reactor can be sealed after addition of the alcohol and the initiator and prior to heating. The gaseous starting compound can then be added at a desired reaction temperature, either continuously or in portions, until a stoichiometric (or greater) amount of starting compound has been added or until the reaction rate has slowed significantly.

After completion of starting compound addition, or after the reaction has run to completion, the reactor can be cooled and vented and the contents purified by, for example, distillation. Generally, the reaction can be run for a period of time equivalent to about ten half lives of the free radical initiator. Alternatively, a free radical quencher (for example, ascorbic acid) can be added to decompose any remaining initiator prior to purification. Those skilled in the art will recognize that the optimum process conditions and procedure for a particular reaction will be determined by the nature of the selected starting compound, alcohol, and initiator. Free radical addition reactions of this type have been described, for example, by Costa et al. in J. Macromol. Sci.-Chem., A18(2), 299 (1982), the description of which is incorporated herein by reference.

The anionic addition reaction can be effected by combining the perfluoroolefin or perfluorovinyl ether starting compound and the fluoroalcohol intermediate (or the starting alcohol) in the presence of at least one anionic addition catalyst (for example, a Lewis base). Useful catalysts include potassium carbonate, cesium carbonate, potassium fluoride, potassium hydroxide, potassium methoxide, triethylamine, trimethylamine, potassium cyanate, potassium bicarbonate, sodium carbonate, sodium bicarbonate, cesium fluoride, potassium bifluoride, potassium acetate, and the like, and mixtures thereof; with potassium carbonate, potassium bicarbonate, and mixtures thereof being preferred.

The reactants and catalyst can be combined in a reactor (for example, a pressure reactor) in any order, and the reaction can be run at a desired temperature (for example, from about 30° C. to about 50° C.) under the above-described conditions of pressure and agitation. Generally, however, use of a non-reactive, polar solvent (for example, acetonitrile, tetrahydrofuran, glyme, or a mixture of two or more thereof) can facilitate the reaction. The resulting product can be purified by, for example, distillation. Olefinic reaction by-products can be removed by reaction with a reagent that will preferentially react with the olefinic double bond. Such reagents include, for example, anhydrous hydrogen fluoride; potassium bifluoride in a polar, aprotic solvent, with or without a phase transfer catalyst; potassium permanganate in acetone; and elemental bromine with or without irradiation. Anionic addition reactions of this type have been described, for example, in U.S. Pat. No. 3,962,348 (Benninger et al.), International Patent Publication No. WO 02/102858 (Honeywell International, Inc.), and by K. Chi and G. Furin in Bull. Korean Chem. Soc. 20(2), 220 (1999), the descriptions of which are incorporated herein by reference.

Preferably, the free radical addition reaction is carried out first, followed by the anionic addition. When a polyfunctional alcohol is utilized, however, the two types of addition reactions can be carried out in either order, provided that, when the anionic addition reaction is carried out first, the ratios of the reactants are controlled such that the main reaction product is the desired first fluoroalcohol intermediate. (When the anionic addition reaction is carried out first with a polyfunctional alcohol, the process also generally involves a third addition reaction (anionic in type) to convert a second fluoroalcohol intermediate (resulting from the second addition reaction, which is free radical in type) to the desired hydrofluoroether compound.) The process of the invention can therefore enable the production of a wide variety of different hydrofluoroether compounds by varying the order of the addition steps and the nature of the reactants.

Use of Hydrofluoroether Compounds

The hydrofluoroether compounds of the invention (or a normally liquid composition comprising, consisting, or consisting essentially thereof) can be used in various applications where the aforementioned CFCs have been used. For example, the compounds can be used as solvents for precision or metal cleaning of electronic articles such as disks or circuit boards; as heat transfer agents; as cell size regulators in making foam insulation (for example, polyurethane, phenolic, and thermoplastic foams); as chemical fire extinguishing agents in streaming applications; as carrier fluids or solvents for document preservation materials and for lubricants; as power cycle working fluids such as for heat pumps; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists when used with, for example, a chlorohydrocarbon such as 1,1,1-trichloroethane or trichloroethylene.

The hydrofluoroether compounds typically exhibit high dielectric strengths (for example, greater than about $10^8$ ohm-cm), which can make them well-suited for use in the semiconductor industry. The hydrofluoroether compounds (for example, $CF_3CFHCF_2CH(CH_3)OCF_2CFHCF_3$) that exhibit unexpectedly high thermal stabilities can be particularly useful in high temperature applications such as in heat transfer applications in the semiconductor industry and in flat screen panel manufacture.

The hydrofluoroether compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents can be chosen to modify or enhance the properties of a composition for a particular use and can be utilized in ratios (of co-solvent(s) to hydrofluoroether(s)) such that the resulting composition preferably has no flash point. If desired, the hydrofluoroether compounds can be used in combination with other compounds that are very similar in properties relative to a particular use (for example, other hydrofluoroether compounds) to form compositions that "consist essentially" of the hydrofluoroether compounds of the invention.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The hydrofluoroether compounds are useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.), the descriptions of which are incorporated herein. Both organic and inorganic substrates can be cleaned by contacting them with a composition comprising at least one HFE of the invention. Most contaminants can be removed, including hydrocarbon contaminants, fluorocarbon contaminants, particulates, and water.

In using the compounds for the drying of or displacing water from the surface of articles (such as circuit boards), the process of drying or water displacement described in, for example, U.S. Pat. No. 5,125,978 (Flynn et al.) can be used. Broadly, such process comprises contacting the surface of an article with a liquid composition comprising at least one hydrofluoroether compound of the invention, preferably in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978, which description is incorporated herein.

In using the compounds of the invention in vapor phase soldering, the process described in, for example, U.S. Pat. No. 5,104,034 (Hansen) can be used, which description is incorporated herein. Briefly, such process comprises immersing a component to be soldered in a body of vapor comprising at least one hydrofluoroether compound of this invention to melt the solder. In carrying out such a process, a liquid pool of a hydrofluoroether composition is heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the compounds of the invention as cell size regulators in making plastic foam (such as foamed polyurethane), the process reactants and reaction conditions described in, for example, U.S. Pat. No. 5,210,106 (Dams et al.) and U.S. Pat. No. 5,539,008 (Dams et al.) can be used, which descriptions are incorporated herein. One such process comprises vaporizing a blowing agent mixture in the presence of at least one foamable polymer or the precursors of at least one foamable polymer, the blowing agent mixture comprising at least one hydrofluoroether compound of the invention.

In using the compounds of the invention as heat transfer agents, the processes described in, for example, U.S. Reissue Pat. No. 37,119 E (Sherwood) and U.S. Pat. No. 6,374,907 B1 (Tousignant et al.) can be used, which descriptions are incorporated herein. In carrying out such processes, heat is transferred between a heat source (for example, a silicon wafer or a component of a flat panel display) and a heat sink through the use of a heat transfer agent comprising at least one hydrofluoroether compound of the invention. Unlike some HFEs that are used as heat transfer agents, the HFEs of the invention are not mixtures of components of widely disparate molecular weights. Rather, the HFEs are generally monodisperse (that is, of a single molecular weight). This means that their physical properties remain relatively constant over time, thereby avoiding significant heat transfer performance deterioration. In addition, the HFEs of the invention generally exhibit a wide liquid range, useful viscosity over that range, and relatively high thermal stability at end use temperatures, making them well-suited for use as heat transfer fluids.

In using the hydrofluoroether compounds of the invention as deposition solvents in coating applications or in document preservation applications, the processes described in, for example, U.S. Pat. No. 5,925,611 (Flynn et al.) and U.S. Pat. No. 6,080,448 (Leiner et al.) can be used, which descriptions are incorporated herein. Such processes for depositing a coating on a substrate (for example, magnetic recording media or cellulose-based materials) comprises applying, to at least a portion of at least one surface of the substrate, a composition comprising (a) a solvent composition comprising at least one hydrofluoroether compound of the invention; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Preferred materials include perfluoropolyether, hydrocarbon, and silicone lubricants; amorphous copolymers of tetrafluoroethylene; polytetrafluoroethylene; document preservation materials; and combinations thereof. Most preferably, the material is a perfluoropolyether or a document preservation material.

In using the hydrofluoroether compounds of the invention as fire extinguishing and prevention agents, the processes described in, for example, U.S. Pat. No. 5,718,293 (Flynn et al.) can be used, which descriptions are incorporated herein. Such process for the extinction of fires comprises applying or introducing to a fire a composition comprising at least one hydrofluoroether compound of the invention. The HFEs of the invention can be used alone or in combination with other commonly-used fire extinguishing or prevention agents.

In using the hydrofluoroether compounds of the invention in cutting or abrasive working operations, the processes described in, for example, U.S. Pat. No. 6,759,374 (Milbrath et al.) can be used, the descriptions of which are incorporated herein. Such a process for metal, cermet, or composite working comprises applying a working fluid to a metal, cermet, or composite workpiece and tool, the working fluid comprising at least one hydrofluoroether compound of the invention and at least one lubricious additive. The working fluid can further comprise one or more conventional additives (for example, corrosion inhibitors, antioxidants, defoamers, dyes, bactericides, freezing point depressants, metal deactivators, co-solvents, and the like, and mixtures thereof).

In using the hydrofluoroether compounds of the invention as polymerization media or as chain transfer agents, the processes described in, for example, Research Disclosures, Number 40576, page 81 (January 1998) and in U.S. Pat. No. 5,182,342 (Feiring et al.) and U.S. Pat. No. 6,399,729 (Farnham et al.) can be used, the descriptions of which are incorporated herein. Such processes comprise polymerizing at least one monomer (preferably, at least one fluorine-containing monomer) in the presence of at least one polymerization initiator and at least one hydrofluoroether compound of the invention.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Aldrich Chemical Company, Milwaukee, Wis. unless otherwise noted.

In the following examples, mixtures of diastereomers were obtained due to the presence of two (or more) optical centers in the molecules. These diastereomers had boiling points that were very close together, and thus the diastereomers were not separated by distillation. In many cases, however, such diastereomers can be easily separated by gas chromatography.

Test Methods

Nuclear Magnetic Resonance (NMR)

$^1$H and $^{19}$F NMR spectra were run on a Varian UNITYplus 400 fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Viscosity Measurement

Kinematic viscosities were measured using Ubbelohde glass capillary viscometers (available from Cannon Instrument Co., State College, Pa.) and a SCHOTT AVS350 viscometer timer (available from Schott North America, Elmsford, N.Y.). Temperature was controlled using a Lawler temperature control bath (available from Lawler Manufacturing Company, Inc., Indianapolis, Ind.) filled with NOVEC-7500 (a hydrofluoroether; available from 3M Company, St. Paul, Minn.). The Lawler bath was cooled by a JULABO F-83 refrigerated circulator (available from Julabo USA, Allentown, Pa.).

Flashpoint Measurement

Closed cup flashpoints were measured using the ASTM (American Society for Testing of Materials) Test Method D-3278-96 e-1, "Flash Point of Liquids by Small Scale Closed-Cup Apparatus."

| Table of Abbreviations | |
|---|---|
| Abbreviation or Trade Designation | Description |
| HFP | hexafluoropropene |
| LUPEROX 575 | t-amyl peroxy-2-ethylhexanoate free radical initiator, commercially available from Arkema, Crosby, TX |
| ADOGEN 464 | phase transfer catalyst, methyltrialkyl ($C_8$-$C_{10}$) ammonium chloride, 49% solution in anhydrous diglyme |

-continued

Table of Abbreviations

| Abbreviation or Trade Designation | Description |
|---|---|
| HFP dimer | $CF_3CF=CFCF(CF_3)_2$ |
| b.p. | Boiling point, measured at ambient pressure unless otherwise specified |
| b.r. | Boiling range, measured at ambient pressure unless otherwise specified |

Example 1

Preparation of $C_3F_7OCFHCF_2CH_2OCF_2CFHCF_3$ $C_3F_7OCFHCF_2CH_2OH$ was prepared by the reaction of $C_3F_7OCF=CF_2$ (53 g, 0.2 mol) with methanol (63.7 g, 2.0 mol) using t-amylperoxybenzoate (1.0 g) as free radical initiator at 106° C. The product reaction mixture was washed with water and distilled and the distillation fraction of b.r.=115-117° C. used in the next step.

$C_3F_7OCFHCF_2CH_2OH$ (18.5 g, 0.062 mol), potassium carbonate (1.67 g, 0.012 mol), and anhydrous acetonitrile (73.1 g) were placed in a 500 mL round bottom flask equipped with a magnetic stir bar, a gas inlet tube, and a solid carbon dioxide/acetone condenser. The resulting reaction mixture was heated while stirring to 45° C., and addition of HFP (10 g) through the gas inlet tube was begun. After 10 minutes, the internal temperature of the reaction mixture reached 54° C., and the addition of HFP was halted. After cooling back to 45° C., an additional 10 g of HFP was added. After stirring for 16 hours at room temperature, the mixture was poured into a separatory funnel. The resulting lower fluorochemical phase was separated and washed once with brine, and the resulting lower phase was separated to yield 25.1 g. GCMS analysis of this material showed that it contained about 61% of the product hydrofluoroether $C_3F_7OCFHCF_2CH_2OCF_2CFHCF_3$ and 21% of several olefins formed by loss of one or two moles of hydrogen fluoride (HF) from the parent compound. Treatment of this mixture with anhydrous HF did not result in HF addition to the olefin; no reaction occurred.

19.2 g of the ether/olefin mixture was treated with 4.5 g potassium bifluoride ($KHF_2$), 3.0 g of a 50% by weight solution of ADOGEN 464 in anhydrous diglyme, and solvent diglyme (55.4 g) at 110° C. for 16 hours. The resulting reaction mixture was poured into water, and the resulting lower fluorochemical phase was separated and then distilled in a concentric tube fractionating unit (Ace Glass Catalog Number 9331, Ace Glass Inc., Vineland, N.J.). The resulting distillate was washed with water to remove the co-distilled diglyme to provide a product having about 94% product hydrofluoroether and 6% remaining olefins.

Example 2

Preparation of $CF_3CFHCF_2CH_2OCF_2CFHCF_3$

Methanol (150.0 g, 4.68 mol) and LUPEROX 575 (6 g, 0.024 mol) were combined in a 600 mL Parr reactor. HFP was added at a continuous rate at a temperature of 75° C. to the reactor until a total of 190.0 g (1.26 mol) had been added. The resulting reaction mixture was then stirred for 16 hours at 75° C. to destroy any remaining free radical initiator. The contents of the reactor were then emptied and excess methanol was removed through rotary evaporation.

The resulting product alcohol $CF_3CFHCF_2CH_2OH$ (228 g, 1.25 mol) was then combined with potassium carbonate (17.3 g, 0.125 mol) and acetonitrile (100 mL) in a 600 mL Parr reactor. The temperature was set to 40° C., and HFP was added at a continuous rate to a total amount of 206 g (1.37 mol). The reactor contents were emptied, and the acetonitrile solvent was removed through rotary evaporation. Of the 145.6 g of recovered product, approximately 50% was the olefin of the desired product ($CF_3CFHCF_2CH_2OCF=CFCF_3$). This olefin was removed by reaction with potassium bifluoride (20 g, 0.25 mol) in a 600 mL Parr reactor using diglyme as a solvent (100 mL) and a small amount of ADOGEN 464 (5 g) as a phase transfer catalyst at 110° C. for 24 hours. The reactor contents were then emptied, and the diglyme was removed through washing with water. The resulting crude material was fractionated using a concentric tube column (b.p.=118° C., 97%). GCMS data was obtained and was consistent with the above hydrofluoroether structure.

Example 3

Preparation of $CF_3CFHCF_2CH(CH_3)OCF_2CFHCF_3$

Ethanol (100 g, 2.17 mol) and LUPEROX 575 (6 g, 0.024 mol) were combined in a 600 mL Parr reactor. The temperature of the reactor was set to 75° C., and HFP was added at a continuous rate up to a total amount of 202.5 g (1.35 mol). The resulting reaction mixture was allowed to stir for 16 hours at 75° C. to destroy remaining free radical initiator. The resulting alcohol was purified using a 10-plate Oldershaw perforated plate column (b.p.=120° C., 97%).

200 g of this alcohol were combined with potassium carbonate (14.7 g, 0.102 mol) and 100 mL of acetonitrile in a 600 mL Parr reactor. The reactor temperature was set to 35° C., and HFP was added at a continuous rate for a total of 170 g (1.13 mol). The reactor contents were emptied, and the acetonitrile was removed through rotary evaporation. The resulting product contained the olefin of the desired hydrofluoroether, which was removed through treatment with anhydrous HF at room temperature (essentially as described in U.S. Patent Publication No. 2005/0127322 (Costello et al.)). The resulting material was then fractionated using a 10-plate Oldershaw column (purity=99%, b.p.=130° C.). Viscosity measurements, GCMS data, and NMR spectra were obtained. The viscosity of the material was $1.4 \times 10^{-5}$ $m^2/s$ (14 centistokes) at −50° C., and the GCMS and NMR ($^{1}H$ and $^{19}F$) results confirmed the above hydrofluoroether product structure.

Example 4

Preparation of $CF_3CFHCF_2C(CH_3)_2OCF_2CFHCF_3$

Isopropanol (200.0 g, 3.32 mol) and LUPEROX 575 (6 g, 0.024 mol) were combined in a 600 mL Parr reactor. The temperature of the reactor was set at 75° C. HFP was added at a continuous rate to the reactor for a total of 327.2 g (2.2 mol). The resulting reaction mixture was allowed to stir for 16 hours at 75° C. to destroy remaining free radical initiator. The reactor contents were then emptied, and excess isopropanol was removed by rotary evaporation. The resulting product alcohol was then fractionated using a 10-plate Oldershaw column.

100 g (0.47 mol) of the purified alcohol (99%, b.p.=127° C.) were added to a 600 mL Parr reactor with potassium carbonate (6.5 g, 0.047 mol) and acetonitrile (200 mL). The reactor temperature was set to 35° C., and HFP was added at a continuous rate to the reactor to a total of 77.5 g (0.51 mol, 10% excess). The reactor contents were emptied, and the acetonitrile was removed by rotary evaporation. The resulting product was then distilled using a concentric tube column. Samples of the resulting purified product (99%, b.p.=140° C.) were tested by viscosity measurement, GCMS, NMR, and flashpoint measurement, essentially as described above. The viscosity of the purified product was $1.8 \times 10^{-5}$ m$^2$/s (18 centistokes) at −50° C., and its flashpoint was measured as 54° C. (130° F.) GCMS and NMR ($^1$H and $^{19}$F) confirmed the above hydrofluoroether product structure.

Example 5

Preparation of $CF_3CFHCF_2C(CH_3)_2$ $OCF_2CFHOCF_2CF_2CF_3$

Isopropanol (200.0 g, 3.32 mol) and LUPEROX 575 (6 g, 0.024 mol) were combined in a 600 mL Parr reactor. The reactor temperature was set at 75° C. HFP was added at a continuous rate to the reactor until the pressure began to increase, to a total of 327.2 g (2.2 mol). The resulting reaction mixture was allowed to stir for 16 hours at 75° C. to destroy remaining free radical initiator. The reactor contents were then emptied, and excess isopropanol was removed by rotary evaporation. The resulting product alcohol was then fractionated using a 10-plate Oldershaw column.

100 g (0.47 mol) of the resulting purified alcohol (99%, b.p.=127° C.) was added to a 600 mL Parr reactor with potassium carbonate (6.5 g, 0.047 mol), acetonitrile (200 mL), and perfluoropropylvinylether ($C_3F_7OCF=CF_2$, 109 g, 0.52 mol). The reactor temperature was set to 40° C., and the resulting reaction mixture was allowed to stir for 16 hours, during which time the pressure on the reactor dropped to zero. The reactor contents were emptied, and the acetonitrile was removed through rotary evaporation. The resulting product was purified using a concentric tube column. Samples of the purified product (99%, b.p.=171° C.) were tested by viscosity measurement, GCMS, NMR, and flashpoint measurement, essentially as described above. The viscosity of the purified product was $5.7 \times 10^{-5}$ m$^2$/s (57 centistokes) at −50° C., and no flashpoint was observed. GCMS and NMR ($^1$H and $^{19}$F) confirmed the above hydrofluoroether product structure.

Example 6

Preparation of $CF_3CF(CH_2OCF_2CFHCF_3)CFHCF$ $(CF_3)_2$ and $CF_3CFH(CH_2OCF_2CFHCF_3)CFCF$ $(CF_3)_2$ HFP dimer (106.5 g, 0.35 mol), LUPEROX 575 (6 g, 0.024 mol), and methanol (200 g, 6.25 mol) were combined in a 600 mL Parr reactor. The temperature of the reactor was set to 75° C., and the resulting reaction mixture was stirred for 16 hours. The reactor contents were emptied, and the excess methanol was removed by rotary evaporation.

The resulting product alcohol (100 g, 0.03 mol) was combined with potassium carbonate (4.1 g, 0.03 mol) and acetonitrile (150 mL) in a 600 mL Parr reactor. The reactor temperature was set to 40° C., and HFP was added to the reactor at a continuous rate up to a total of 50 g (0.33 mol). The reactor contents were emptied, and the acetonitrile was removed through rotary evaporation. The olefin of the desired hydrofluoroether product was present and was removed by reaction with anhydrous HF at room temperature. The resulting product was distilled using a concentric tube column (b.p.=155° C.; 93% desired product in approximately a 50/50 mixture of the two isomers shown above). GCMS and NMR ($^1$H and $^{19}$F) confirmed the above hydrofluoroether product structures.

Example 7

Preparation of $CF_3CFHCF_2CH(OCF_2CFHCF_3)$ $CH_2OCF_2CFHCF_3$

Ethylene glycol (1.0 mol) and LUPEROX 575 (5 g, 0.02 mol) are combined in a 600 mL Parr reactor. The temperature of the reactor is set to 75° C., and HFP (1.1 mol) is added to the reactor at a continuous rate. The resulting reaction mixture is allowed to stir at this temperature for 16 hours. The resulting crude reaction material is distilled under vacuum to afford $CF_3CFHCF_2CH(OH)CH_2OH$ as a mixture of diastereomers.

The resulting diol (1.0 mol) is combined in a reactor with potassium carbonate (0.1 mol) and acetonitrile (100 mL) and heated to 40° C. HFP (2.19 mol) is added at a continuous rate to the reactor, and the resulting reaction mixture is stirred for 18 hours at 40° C. The reactor contents are emptied, and the acetonitrile is removed through rotary evaporation. The resulting product contains dehydrofluorinated olefins of the desired hydrofluoroether product, which are converted by reaction with anhydrous HF at room temperature to the diether product. The product is fractionated using a concentric tube column.

Example 8

Preparation of $CF_3CFHCF_2CH_2OCF_2CFHOC_3F_7$

Hexafluorobutanol, $CF_3CFHCF_2CH_2OH$ (75 g, prepared essentially as described in Example 2), was combined with potassium carbonate (11.4 g, 0.082 mol), $C_3F_7OCF=CF_2$ (120.5 g, 0.45 mol), and 100 mL of acetonitrile in a 600 mL Parr reactor. The temperature of the reactor was raised to 45° C., and the resulting reaction mixture was stirred for about 96 hours. The reactor was cooled and the contents of the reactor poured into water. The resulting lower phase was separated and washed two more times with an equal volume of water. The resulting product (98.5% pure by gas/liquid chromatography (GLC), 150 g) was distilled using a concentric tube column, with the product cut boiling at 144-146° C. The structure of the product was confirmed by GCMS. The approximately 1% olefins that were formed in the reaction were removed essentially as described above by reaction with potassium bifluoride in diglyme.

Example 9

Preparation of $CF_3CFHCF_2CH_2OCF_2CFHOCF_3$

Hexafluorobutanol, $CF_3CFHCF_2CH_2OH$ (65.3 g, 0.34 mol), prepared essentially as described in Example 2) was combined with potassium carbonate (9.9 g, 0.072 mol) and 133 g of acetonitrile in a 600 mL Parr reactor. The temperature of the reactor was raised to 45° C. and $CF_3OCF=CF_2$ (65.6 g, 0.39 mol) added as a gas over about two hours. The resulting reaction mixture was stirred for about 18 hours at 45° C. The reactor was cooled and the contents of the reactor filtered to remove the potassium carbonate. The resulting product-containing filtrate was distilled using a concentric tube column, with the product cut boiling at 115-119° C. The product structure was confirmed by GCMS.

Example 10

Preparation of $CF_3OCF(CF_3)CF_2OCFHCF_2C(CH_3)_2OCF_2CFHCF_3$ $CF_3OCF(CF_3)CF_2OCFHCF_2C(CH_3)_2OH$ was prepared by the reaction of $CF_3OCF(CF_3)CF_2OCF=CF_2$ (52.9 g, 0.16 mol) with isopropanol (202 g, 3.37 mol) using LUPEROX 575 (11.4 g) as free radical initiator at 75° C. The resulting product reaction mixture was distilled and the distillation fraction of b.r.=161-166° C. used in the next step.

$CF_3OCF(CF_3)CF_2OCFHCF_2C(CH_3)_2OH$ (37.6 g, 0.096 mol), potassium carbonate (4.4 g, 0.032 mol), and anhydrous acetonitrile (144 g) were placed in a 600 mL Parr reaction vessel, which was sealed and heated to 45° C. HFP (34.7 g, 0.23 mol) was added to the vessel as a gas over about one hour and the resulting reaction mixture held, while stirring, for 18 hours at 45° C. After cooling the reaction vessel to room temperature and venting the excess HFP, the reaction vessel was opened, the reaction mixture was filtered to remove the potassium carbonate, and most of the acetonitrile solvent was removed by rotary evaporation. The resulting residue was then distilled in a concentric tube column with the main fraction boiling at 186° C. in greater than 90% purity. The above-shown product structure was confirmed by GCMS.

Example 11

Preparation of $CF_3CFHCF_2CH(CH_3)OCF_2CFHOC_3F_7$

Ethanol (100.0 g, 2.17 mol) and LUPEROX 575 (10.6 g, 0.434 mol) were combined in a 600 mL reactor. The temperature of the reactor was set at 75° C. HFP was added at a continuous rate to the reactor until the pressure began to increase, to a total of 181.0 g (1.2 mol). The resulting reaction mixture was allowed to stir for 16 hours at 75° C. to destroy remaining free radical initiator. The mixture was poured into a separatory funnel, and the resulting lower fluorochemical phase was separated and washed five-fold with water. The resulting lower phase was separated and one-plate distilled to yield 90.0 g boiling between 120-129° C. Analysis by gas chromatography showed this material contained 92.0% of the desired product alcohol, $CF_3CFHCF_2CH(CH_3)OH$.

The resulting product alcohol (90.0 g, 0.46 mol) was combined with potassium carbonate (0.62 g, 0.004 mol) and acetonitrile (300 mL) in a 600 mL Parr reactor. The reactor was heated to about 82° C., and 100 mL of material was distilled from the reactor to remove water present initially in the acetonitrile or potassium carbonate. The reactor was cooled to room temperature, and perfluoropropyl vinyl ether ($C_3F_7OCF=CF_2$, 122.9 g, 0.46 mol) was added. The reactor was sealed, heated to 40° C., and its contents stirred for 16 hours. Analysis by gas chromatography showed no reaction took place. An additional charge of potassium carbonate (6.2 g, 0.045 mol) was added to the reactor and the contents stirred for an additional 16 hours at 40° C. The reactor contents were then emptied, and the acetonitrile was removed through rotary evaporation. The resulting reaction mixture was washed with water and the resulting lower fluorochemical phase separated. The olefin of the desired hydrofluoroether product was present and was removed by treatment with anhydrous HF at room temperature. The resulting product was distilled using a concentric tube column (b.p.=154° C., 86.6 g, 99.4% desired). GCMS confirmed the above hydrofluoroether structure.

Example 12

Preparation of $C_3F_7OCFHCF_2CH(OCF_2CFHCF_3)CH_3$

Ethanol (50 g, 1.08 mol), LUPEROX 575 (7 g, 0.028 mol), and perfluoropropylvinylether (290 g, 1.09 mol) were combined in a 600 mL Parr reactor. The temperature of the reactor was set to 75° C., and the resulting reaction mixture was stirred for 16 hours. The reactor was then emptied and excess ethanol was removed by washing with three 250 mL portions of distilled water.

The resulting product alcohol, ($C_3F_7OCFHCF_2CH(OH)CH_3$; 216 g, 0.7 mol) was combined with potassium carbonate (9.6 g, 0.07 mol) and acetonitrile (100 mL) in a 600 mL Parr reactor. The temperature of the reactor was set to 35° C. and hexafluoropropene was added at a continuous rate up to a total of 115.5 g (0.77 mol). The resulting reaction mixture was stirred for 2 hours at this temperature. The reactor contents were emptied, and the potassium carbonate removed through filtration. The acetonitrile solvent was removed through rotary evaporation. The resulting material contained the olefin of the desired ether, which was converted to the final product through reaction of the material (100 g, 0.24 mol) with potassium bifluoride (15 g, 0.19 mol) using diglyme as a solvent (100 mL) and a small amount of ADOGEN 464 (5 g) as a phase transfer catalyst at 110° C. for 24 hours in a 600 mL Parr reactor. The reactor contents were then emptied, and diglyme was removed by washing with water. The resulting ether was purified using a concentric tube column (b.p.=155° C.). The GCMS data were consistent with the above-shown structure.

Example 13

Preparation of $CH_3CH(OCF_2CFHCF_3)CF(CF_3)CF-HCF(CF_3)_2$ and $(CF_3)_2CFCF[CH(OCF_2CFHCF_3)CH_3]CFHCF_3$ Ethanol (60 g, 1.3 mol), LUPEROX 575 (7 g, 0.028 mol), and hexafluoropropene dimer (370 g, 1.23 mol) were combined in a 600 mL Parr reactor. The temperature of the reactor was set to 75° C., and the resulting mixture was stirred for 16 hours. After the initial reaction, an additional charge of LUPEROX 575 was added to the reactor, and the mixture was stirred for an additional 16 hours at 75° C. The reactor was then emptied, and excess hexafluoropropene dimer and ethanol were removed through rotary evaporation.

The resulting product alcohols $CH_3CH(OH)CF(CF_3)CF-HCF(CF_3)_2$ and $(CF_3)_2CFCF[CH(OH)CH_3]CFHCF_3$ (248 g, 0.72 mol) were combined with potassium carbonate (9.9 g, 0.072 mol) and 100 mL of acetonitrile in a 600 mL Parr reactor. The temperature of the reactor was set to 35° C., and hexafluoropropene was added continuously up to a total amount of 118 g (0.78 mol). The resulting mixture was stirred for 6 hours at this temperature. The reactor contents were emptied and potassium carbonate removed through filtration. The acetonitrile solvent was removed through rotary evaporation. The resulting product ether was purified using a concentric tube column (b.p.=165° C.). GCMS data were consistent with the above-indicated structures (in about a 70/30 ratio).

Example 14

Preparation of CF$_3$CFHCF[CH(OCF$_2$CFHCF$_3$)CH$_3$]CF$_2$CF$_3$ and CF$_3$CF$_2$CFHCF[CH(OCF$_2$CFHCF$_3$)CH$_3$]CF$_3$ Ethanol (100 g, 2.17 mol), LUPEROX 575 (7 g, 0.028 mol), and perfluoro-2-pentene (153 g, 0.612 mol) were combined in a 600 mL Parr reactor and heated to 75° C. for 16 hours. After the initial reaction, an additional charge of LUPEROX 575 was added to the reactor, and the resulting mixture was stirred for an additional 16 hours at 75° C. The reactor contents were then emptied and ethanol was removed through two 250 mL water washes.

The resulting product alcohols CF$_3$CFHCF[CH(OH)CH$_3$]CF$_2$CF$_3$ and CF$_3$CF$_2$CFH[CH(OH)CH$_3$]CFCF$_3$ (in about a 50/50 ratio) (165 g, 0.55 mol) were combined with potassium carbonate (9 g, 0.065 mol) and 150 mL of acetonitrile in a 600 mL Parr reactor. Hexafluoropropene was added continuously at a temperature of 35° C. up to a total amount of 105 g (0.7 mol). The resulting reaction mixture was stirred for 30 minutes and then emptied and the potassium carbonate removed through filtration. The acetonitrile solvent was removed through rotary evaporation. The resulting product contained the olefin of the desired ether, which was converted to the final product through treatment with anhydrous HF at room temperature. The product was then fractionated using a concentric tube column (purity=99%, b.p.=155° C., Viscosity (-50° C.) 8.5×10$^{-5}$ m$^2$/s (85 centistokes)). GCMS data were consistent for the above-indicated structures.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A hydrofluoroether compound consisting of two terminal fluoroalkyl groups and an intervening oxymethylene group, each of said fluoroalkyl groups having only one hydrogen atom and, optionally, at least one catenated heteroatom, and said oxymethylene group being unsubstituted or being substituted by having at least one carbon-bonded hydrogen atom replaced with an alkyl or fluoroalkyl group that optionally contains at least one catenated heteroatom; with the proviso that said hydrogen atom is part of a monofluoromethylene moiety; wherein said compound is one of a class that is represented by the following general formula (I):

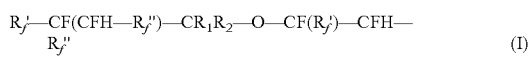

wherein each R$_f'$ is independently a fluorine atom or a perfluoroalkyl group that is linear, branched, cyclic, or a combination thereof and that optionally contains at least one catenated heteroatom; each R$_f''$ is independently a perfluoroalkyl group that is linear, branched, cyclic, or a combination thereof and that optionally contains at least one catenated heteroatom, and R$_1$ and R$_2$ are independently a hydrogen atom, an alkyl group that is linear, branched, cyclic, or a combination thereof and that optionally contains at least one catenated heteroatom, or a fluoroalkyl group that is linear, branched, cyclic, or a combination thereof and that optionally contains at least one catenated heteroatom.

2. The hydrofluoroether compound of claim 1, wherein said oxymethylene group is substituted.

3. The hydrofluoroether compound of claim 2, wherein at least one carbon bonded hydrogen atom of said oxymethylene group is replaced with an alkyl group that optionally contains at least one catenated heteroatom.

4. The hydrofluoroether compound of claim 2, wherein at least one carbon bonded hydrogen atom of said oxymethylene group is replaced with a fluoroalkyl group that optionally contains at least one catenated heteroatom.

5. The hydrofluoroether compound of claim 1, wherein said R$_1$ is hydrogen or an alkyl group that is linear, branched, cyclic, or a combination thereof; and said R$_2$ is hydrogen or an alkyl group that is linear, branched, cyclic, or a combination thereof, or is —(CR$_1$R$_3$)$_n$—O—CF(R$_f'$)—CFH—R$_f''$, wherein R$_3$ is hydrogen or an alkyl group that is linear, branched, cyclic, or a combination thereof, or is —CF(R$_f'$)—CFH—R$_f''$, and n is an integer of 1 to about 8.

6. The hydrofluoroether compound of claim 5, wherein said R$_2$ is an alkyl group that is linear, branched, cyclic, or a combination thereof.

7. The hydrofluoroether compound of claim 6, wherein said R$_1$ is hydrogen or methyl, and said R$_2$ is methyl.

8. The hydrofluoroether compound of claim 1, wherein said compound is selected from

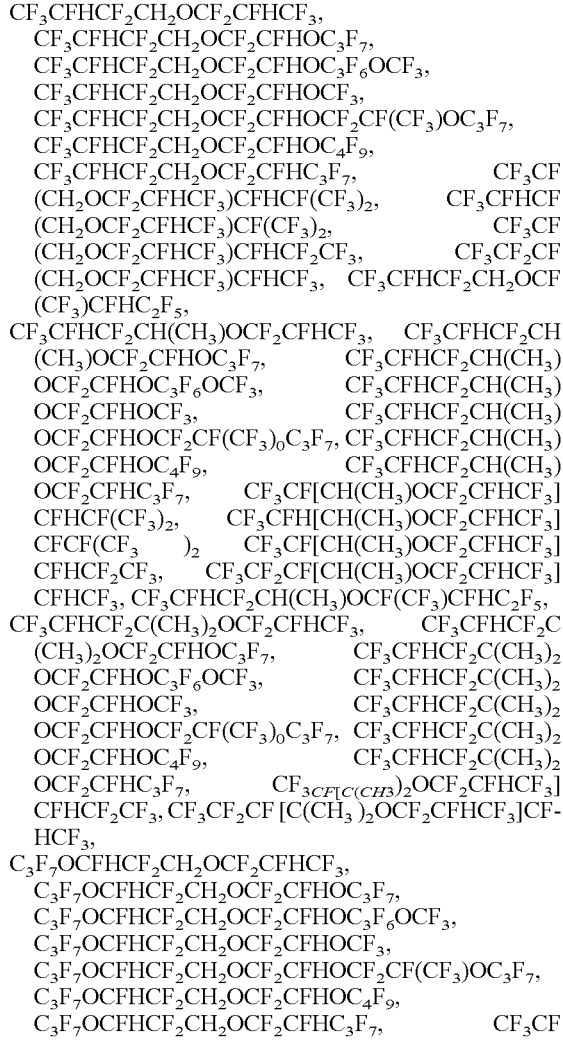

(CH₂OCF₂CFHOC₃F₇)CFHCF(CF₃)₂, CF₃CF(CH₂OCF₂CFHOC₃F₇)CFHCF₂CF₃, CF₃CF₂CF(CH₂OCF₂CFHOC₃F₇)CFHCF₃,
C₃F₇OCFHCF₂CH(CH₃)OCF₂CFHCF₃,
C₃F₇OCFHCF₂CH(CH₃)OCF₂CFHOC₃F₇,
CF₃OCFHCF₂CH(CH₃)OCF₂CFHOC₃F₆OCF₃,
C₃F₇OCFHCF₂CH(CH₃)OCF₂CFHOCF₃,
CF₃OCFHCF₂CH(CH₃)OCF₂CFHOCF₂CF(CF₃)OC₃F₇, C₃F₇OCFHCF₂CH(CH₃)OCF₂CFHOC₄F₉,
C₃F₇OCFHCF₂CH(CH₃)OCF₂CFHC₃F₇, CF₃CF(CH(CH₃)OCF₂CFHOC₃F₇)CFHCF(CF₃)₂, CF₃CF(CH(CH₃)OCF₂CFHOC₃F₇)CFHCF₂CF₃, CF₃CF₂CF(CH(CH₃)OCF₂CFHOC₃F₇)CFHCF₃,
C₃F₇OCFHCF₂C(CH₃)₂OCF₂CFHCF₃,
C₃F₇OCFHCF₂C(CH₃)₂OCF₂CFHOC₃F₇,
C₃F₇OCFHCF₂C(CH₃)₂OCF₂CFHOC₃F₆OCF₃C₃F₇OCFHCF₂C(CH₃)₂OCF₂CFHOCF₃, C₃F₇OCFHCF₂C(CH₃)₂OCF₂CFHOCF₂CF(CF₃)₀C₃F₇,
C₃F₇OCFHCF₂C(CH₃)₂OCF₂CFHOC₄F₉,
C₃F₇OCFHCF₂C(CH₃)₂OCF₂CFHC₃F₇, CF₃CF(C(CH₃)₂OCF₂CFHOC₃F₇)CFHCF(CF₃)₂, CF₃CF(C(CH₃)₂OCF₂CFHOC₃F₇)CFHCF₂CF₃, CF₃CF₂CF(C(CH₃)₂OCF₂CFHOC₃F₇)CFHCF₃,
CF₃CFHCF₂CH(OCF₂CFHCF₃)CH₂OCF₂CFHCF₃, CF₃OCF(CF₃)CF₂OCFHCF₂C(CH₃)₂OCF₂CFHCF₃, [CF₃CFHCF₂OCH(CF₂CFHCF₃)]₂CH₂, CF₃CFHCF₂OCH₂CH₂CH(CF₂CFHCF₃)OCF₂CFHCF₃, C₄F₉CH₂CH(CF₂CFHCF₃)OCF₂CFHCF₃, CH₃C(OCF₂CFHCF₃)(CF₂CFHCF₃)CH₂OCF₂CFHCF₃, CH₃CH(OCF₂CFHCF₃)CH(OCF₂CFHCF₃)CF₂CFHCF₃,

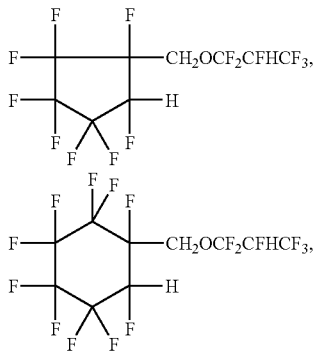

and mixtures thereof.

9. The hydrofluoroether compound of claim 1, wherein said compound is selected from
CF₃CFHCF₂CH(CH₃)OCF₂CFHCF₃,
CF₃CFHCF₂CH₂OCF₂CFHCF₃,
CF₃CFHCF₂CH₂OCF₂CFHOC₄F₉,
C₃F₇OCFHCF₂CH(CH₃)OCF₂CFHCF₃, CF₃CFH[CH(CH₃)OCF₂CFHCF₃]CFCF(CF₃)₂, CF₃CFHCF₂CH(OCF₂CFHCF₃)CH₂OCF₂CFHCF₃,
CF₃CFHCF₂CH₂OCF₂CFHOC₃F₇,
CF₃CFHCF₂CH₂OCF₂CFHOCF₃, CF₃CF(CH₂OCF₂CFHCF₃)CFHCF(CF₃)₂, CF₃CFHCF(CH₂OCF₂CFHCF₃)CF(CF₃)₂, CF₃CFHCF₂CH(CH₃)OCF₂CFHOC₃F₇,
CF₃CF[CH(CH₃)OCF₂CFHCF₃]CFHCF(CF₃)₂, CF₃CF[CH(CH₃)OCF₂CFHCF₃]CFHCF₂CF₃, CF₃CF₂CF[CH(CH₃)OCF₂CFHCF₃]CFHCF₃, CF₃CFHCF₂C(CH₃)₂OCF₂CFHCF₃, CF₃CFHCF₂C(CH₃)₂OCF₂CFHOC₃F₇, C₃F₇OCFHCF₂CH₂OCF₂CFHCF₃, CF₃OCF(CF₃)CF₂OCFHCF₂C(CH₃)₂OCF₂CFHCF₃, CF₃CFHCF₂OCH₂CH₂CH(CF₂CFHCF₃)OCF₂CFHCF₃, and mixtures thereof.

10. The hydrofluoroether compound of claim 1, wherein said compound is selected from
CF₃CFHCF₂CH(CH₃)OCF₂CFHCF₃, CF₃CFH[CH(CH₃)OCF₂CFHCF₃]CFCF(CF₃)₂, CF₃CF[CH(CH₃)OCF₂CFHCF₃]CFHCF₂CF₃, CF₃CFHCF₂CH(OCF₂CFHCF₃)CH₂OCF₂CFHCF₃, and mixtures thereof.

11. A hydrofluoroether compound that is one of a class that is represented by the following general formula (I):

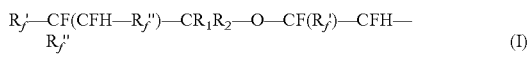

wherein each $R_f'$ is independently a fluorine atom or a perfluoroalkyl group that is linear, branched, cyclic, or a combination thereof each $R_f''$ is independently a perfluoroalkyl group that is linear, branched, cyclic, or a combination thereof and that optionally contains at least one catenated heteroatom; $R_1$ is hydrogen or an alkyl group having up to about three carbon atoms; and $R_2$ is an alkyl group having up to about three carbon atoms.

12. The compound of claim 11, wherein each said $R_f'$ is independently fluorine or $C_3F_7$—; each said $R_f''$ is independently selected from $C_3F_7O$—, $C_4F_9O$—, $C_3F_7OC_3F_6O$—, $CF_3OC_3F_6O$—, and $CF_3$—; said $R_1$ is hydrogen or methyl; and said $R_2$ is methyl.

13. A process for preparing the hydrofluoroether compound of claim 1 comprising
(a) providing (1) at least one perfluoroolefin or perfluorovinyl ether starting compound that optionally contains at least one catenated heteroatom, said perfluoroolefin starting compound containing at least one carbon atom bonded to one of the carbon atoms of its olefinic double bond, and said perfluorovinyl ether starting compound having a terminal difluoromethylene group as part of its olefinic double bond, and (2) at least one hydrocarbon or addition-capable fluorocarbon alcohol that is monofunctional or polyfunctional and that optionally contains at least one catenated heteroatom;
(b) effecting a free radical type of addition reaction or an anionic type of addition reaction of said staffing compound and said alcohol to form at least one first fluoroalcohol intermediate;
(c) providing at least one perfluoroolefin or perfluorovinyl ether finishing compound that is the same as or different from said staffing compound, said perfluoroolefin finishing compound containing at least one carbon atom bonded to one of the carbon atoms of its olefinic double bond, and said perfluorovinyl ether finishing compound having a terminal difluoromethylene group as part of its olefinic double bond; and
(d) effecting an anionic type of addition reaction or a free radical type of addition reaction of said finishing compound and said first fluoroalcohol intermediate to form at least one hydrofluoroether compound of claim 1 or at least one second fluoroalcohol intermediate thereof;
with the proviso that said addition reactions of steps (b) and (d) differ in type; and with the further proviso that, when said alcohol is a monofunctional alcohol, said addition reaction of step (b) is a free radical type addition reaction.

14. The process of claim 13, wherein said alcohol is polyfunctional and said addition reaction of step (b) is a free radical type addition reaction.

15. The process of claim 13, wherein said alcohol is monofunctional.

16. A process for removing a contaminant from an article comprising contacting said article with a composition comprising at least one hydrofluoroether compound of claim 1.

17. A process for the extinction of fires comprising applying to a fire a composition comprising at least one hydrofluoroether compound of claim 1.

18. A process for preparing a foamed plastic comprising vaporizing a blowing agent mixture in the presence of at least one foamable polymer or the precursors of at least one foamable polymer, said blowing agent mixture comprising at least one hydrofluoroether compound of claim 1.

19. A process for vapor phase soldering comprising melting solder by immersing at least one component that comprises said solder in a body of fluorinated liquid vapor that comprises at least one hydrofluoroether compound of claim 1.

20. A process for transferring heat comprising transferring heat between a heat source and a heat sink through the use of a heat transfer agent comprising at least one hydrofluoroether compound of claim 1.

21. A process for depositing a coating on a substrate comprising applying to at least a portion of at least one surface of said substrate a composition comprising (a) a solvent composition comprising at least one hydrofluoroether compound of claim 1; and (b) at least one coating material that is soluble or dispersible in said solvent composition.

22. A process for cutting or abrasive working comprising applying a working fluid to a metal, cermet, or composite workpiece and tool, said working fluid comprising at least one hydrofluoroether compound of claim 1 and at least one lubricious additive.

23. A polymerization process comprising polymerizing at least one monomer in the presence of at least one polymerization initiator and at least one hydrofluoroether compound of claim 1.

* * * * *

UNITED STATES PATENT AND TRADEMARK OFFICE
CERTIFICATE OF CORRECTION

| | | |
|---|---|---|
| PATENT NO. | : 7,691,282 B2 | |
| APPLICATION NO. | : 11/222383 | |
| DATED | : April 6, 2010 | |
| INVENTOR(S) | : Richard Mark Flynn | |

It is certified that error appears in the above-identified patent and that said Letters Patent is hereby corrected as shown below:

Title Page 1, Column 2 Item [56] (Other Publications)
Line 1; Delete "Chemisrty" and insert -- Chemistry --, therefor.

Title Page 2, Column 1 Item [56] (Other Publications)
Line 5; Delete "Filed" and insert -- File --, therefor.

Column 6
Line 13-14; Delete "$CF_3CFH[CH(CH_3)OCF_2CFHCF_3]CFCF(CF_3)_2$" and insert
-- $CF_3CFH[CH(CH_3)OCF_2CFHCF_3]CFCF(CF_3)_2$, --, therefor.

Column 19
Line 59; In Claim 1, delete "perfluoroalkvl" and insert -- perfluoroalkyl --, therefor.

Line 62; In Claim 1, delete "periluoroalkyl" and insert -- perfluoroalkyl --, therefor.

Line 64; In Claim 1, delete "heteroatom," and insert -- heteroatom; --, therefor.

Column 20
Line 44-45; In Claim 8, delete "$CF_3CFHCF_2CH(CH_3)OCF_2CFHOCF_2CF(CF_3)_OC_3F_7$," and insert
-- $CF_3CFHCF_2CH(CH_3)OCF_2CFHOCF_2CF(CF_3)OC_3F_7$, --, therefor.

Line 48-49; In Claim 8, delete "$CF_3CFH[CH(CH_3)OCF_2CFHCF_3]CFCF(CF_3)_2$" and insert
-- $CF_3CFH[CH(CH_3)OCF_2CFHCF_3]CFCF(CF_3)_2$, --, therefor.

Column 20
Line 58-59; In Claim 8, delete "$CF_{3CF[C(CH3)2}OCF_2CFHCF_3]CFHCF_2CF_3$," and insert
-- $CF_3CF[C(CH_3)_2OCF_2CFHCF_3]CFHCF_2CF_3$, --, therefor.

Signed and Sealed this
Fourteenth Day of August, 2012

David J. Kappos
*Director of the United States Patent and Trademark Office*

Column 21

Line 18-19; In Claim 8, delete "$C_3F_7OCFHCF_2C(CH_3)_2OCF_2CFHOCF_2CF(CF_3)_OC_3F_7$," and insert -- $C_3F_7OCFHCF_2C(CH_3)_2OCF_2CFHOCF_2CF(CF_3)OC_3F_7$, --, therefor.

Column 22

Line 19; In Claim 11, after "thereof" insert -- ; --.

Line 44; In Claim 13, delete "staffing" and insert -- starting --, therefor.

Line 49; In Claim 13, delete "staffing" and insert -- starting --, therefor.